United States Patent
Cazabuena Bonorino et al.

(10) Patent No.: US 10,508,139 B2
(45) Date of Patent: Dec. 17, 2019

(54) COMPOUND, USE, ANTI-TUMOR PHARMACEUTICAL COMPOSITION, GENE CONSTRUCT FOR POLYPEPTIDE EXPRESSION, PROCESS FOR THE PRODUCTION, PROCESS FOR THE EVALUATION OF TUMOR CELLS, METHOD OF SENSITIZATION OF TUMOR CELLS TO CHEMOTHERAPEUTIC

(71) Applicant: União Brasileira de Educação e Assistência, mantendedora da PUCRS, Porto Alegre (BR)

(72) Inventors: Cristina Beatriz Cazabuena Bonorino, Porto Alegre (BR); Ana Paula Duarte de Souza, Porto Alegre (BR)

(73) Assignee: União Brasileira de Educação e Assistência, mantenedora da PUCRS, Porto Alegro (BR)

( * ) Notice: Subject to any disclaimer, the term of this patent is extended or adjusted under 35 U.S.C. 154(b) by 0 days.

(21) Appl. No.: 14/655,608

(22) PCT Filed: Dec. 27, 2013

(86) PCT No.: PCT/BR2013/000612
§ 371 (c)(1),
(2) Date: Jun. 6, 2016

(87) PCT Pub. No.: WO2014/100883
PCT Pub. Date: Jul. 3, 2014

(65) Prior Publication Data
US 2016/0368955 A1   Dec. 22, 2016

(30) Foreign Application Priority Data
Dec. 28, 2012   (BR) ............................ 102012033804

(51) Int. Cl.
| | | |
|---|---|---|
| *A61K 38/00* | (2006.01) | |
| *C07K 14/47* | (2006.01) | |
| *A61K 38/17* | (2006.01) | |
| *A61K 33/24* | (2019.01) | |
| *A61K 33/40* | (2006.01) | |
| *A61K 45/06* | (2006.01) | |
| *A61K 9/00* | (2006.01) | |
| *G01N 33/50* | (2006.01) | |
| *A61P 35/00* | (2006.01) | |

(52) U.S. Cl.
CPC ............ *C07K 14/47* (2013.01); *A61K 9/0019* (2013.01); *A61K 33/24* (2013.01); *A61K 33/40* (2013.01); *A61K 38/1709* (2013.01); *A61K 45/06* (2013.01); *A61P 35/00* (2018.01); *G01N 33/5011* (2013.01); *A61K 38/00* (2013.01)

(58) Field of Classification Search
None
See application file for complete search history.

(56) References Cited

U.S. PATENT DOCUMENTS

2003/0023071 A1* 1/2003 Guerriero, Jr. .... C07K 14/4703
536/23.5

FOREIGN PATENT DOCUMENTS

WO   200181545   11/2001

OTHER PUBLICATIONS

Yang et al. (Cancer Lett. Aug. 28, 2012;321(2):137-43).*
Markman et al. (J Clin Oncol. Feb. 15, 2001;19(4):1001-7).*
NCBI Reference Sequence: NP_077134.1 downloaded from https://www.ncbi.nlm.nih.gov/protein/13195602?report=genbank&log$=protalign&blast_rank=1&RID=ASTS5KH9014 on Feb. 21, 2017.*
Rutkowski et al. (Biomed Res Int. 2013;2013:162513).*
Buchler et al. (Int J Artif Organs 2011; 34 (2): 134-138).*
Yallapu et al., Journal of Ovarian Research 2010, 3:19.*
Tanimura et al. (The Journal of Biological Chemistry vol. 282, No. 49, pp. 35430-35439, Dec. 7, 2007).*
Mazunnder et al. (Natural Compound-Generated Oxidative Stress: From Bench to Bedside, 2016) (Year: 2016).*
Extended European Search Report corresponding to European Patent Application No. 18197745.5, dated Feb. 13, 2019, 11 pages.
Graner et al. "Heat shock protein 70-binding protein 1 is highly expressed in high-grade gliomas, interacts with multiple heat shock protein 70 family members, and specifically binds brain tumor cell surfaces" Cancer Sci., 100 (10);1870-1879 (2009).
Raynes et al. "Inhibition of Hsp70 ATPase activity and protein renaturation by a novel Hsp70-binding protein" J Biol Chem., 273(49):32883-32888 (1998).
Raynes et al. "increased expression of the Hsp70 cochaperone HspBP1 in tumors" Tumour Biol., 24(6):281-285 (2003).
Shomura et al. "Regulation of Hsp70 function by HspBP1: Structural analysis reveals an alternate mechanisms for Hsp70 nucleotide exchange" Molecular Cell, 17(3):367-379 (2005).

(Continued)

*Primary Examiner* — Sergio Coffa
(74) *Attorney, Agent, or Firm* — Myers Bigel, P.A.

(57) ABSTRACT

The use of HspBP1 protein or part thereof for the preparation of an anti-tumor pharmaceutical composition, and its optional combination with one or more chemotherapeutic agents. A gene construct for the expression of said protein; a production process; a process of evaluation of tumor cells; and a method of sensitization of tumors to chemotherapeutic agents. A new experimental model in vivo and in vitro for the development/evaluation of anti-tumor agents. The pharmaceutical compositions provide anti-tumor action and have high specificity to neoplastic cells, resulting in less cytotoxicity to normal dividing cells, in part as a solution to the drawbacks of currently known chemotherapy therapeutic regimens.

3 Claims, 12 Drawing Sheets
Specification includes a Sequence Listing.

(56) References Cited

OTHER PUBLICATIONS

Souza et al. "HspBP1 levels are elevated in breast tumor tissueand inversely relatedto tumor aggressiveness" Cell Stress Chaperones., 14(4301-310 (2009).
Tanimura et al. "Anticancer Drugs Up-regulate HspBP1 and thereby antagonize the Prosurvival Function of Hsp70 in Tumor Cells" The Journal of Biological Chemistry, 282(49) 35430-35439 (2007).
Yashin et al. "The heat shook-binding protein (HspBPl) protects calls against the. cytotoxic action of the Tag7-Hsp70 complex" J Biol Chem 286(12)10258-10264 (2011).

\* cited by examiner

COMPOUND, USE, ANTI-TUMOR PHARMACEUTICAL COMPOSITION, GENE CONSTRUCT FOR POLYPEPTIDE EXPRESSION, PROCESS FOR THE PRODUCTION, PROCESS FOR THE EVALUATION OF TUMOR CELLS, METHOD OF SENSITIZATION OF TUMOR CELLS TO CHEMOTHERAPEUTIC

CROSS REFERENCE TO RELATED APPLICATIONS

This application claims the benefit of, priority from, and is the US National Phase of International Application No. PCT/BR2013/000612 having an International Filing Date of 27 Dec. 2013, which claims the benefit of and priority from Brazil Patent Application No. 10 2012 033804-1 having a filing date of 28 Dec. 2012.

SEQUENCE LISTING

The instant application contains a Sequence Listing which has been submitted in ASCII format via EFS-Web and is hereby incorporated by reference in its entirety. Said ASCII copy, created on 24 Jun. 2015, is named 48206-019u1-sequence-listing-062415.txt and is 7,931 bytes in size.

BACKGROUND OF THE INVENTION

Technical Field

The present invention is related to the pharmaceutical field. More specifically, the present invention relates to: Hsp70 peptidic binders as anti-tumor therapeutic agents, the use thereof, as well as a pharmaceutical composition containing the same, optionally in combination with other chemotherapeutic agents; to a gene construct for the expression of said binder; to production processes; to a process for the evaluation of tumor cells; and to a method of sensitization of tumors.

Prior Art

In 1962, Ritossa and collaborators, when submitting *Drosophila melanogaster* larvae to temperatures 10 degrees Celsius higher than their usual temperature, observed the activation of specific genes. This treatment was referred to as heat shock and, in 1974, the products of these genes were identified as Heat Shock Proteins (Hsps). Subsequent work demonstrated that these proteins can be induced in all living beings when cells respond to high temperatures and other manifestations of stress by the rapid synthesis of Hsps, being, therefore, proteins having a high degree of phylogenetic conservation.

Hsps are categorized into several families, named according to their molecular weight, thus, Hsp70 means a Hsp protein having 70 kilodaltons (kD), for example. These proteins are produced/induced when cellular stresses, such as high temperatures, disturb the physiology of the organism. The main agents that induce the production of Hsps are temperature elevation, oxidative stress, nutritional deficiency, ultraviolet radiation, chemical agents, viral infections, ischemia and reperfusion damage, exposure to pro-inflammatory mediators and treatment with non-steroidal drugs. Said proteins can be located in different cellular compartments, so that, in normal cell conditions, Hsp70 is located in the endoplasmic reticulum lumen, in addition to the cytoplasm and the nucleus.

Over the course of evolution, the proteins of the Hsp70 family such as, for example, the HspBP1 protein, maintain similarity of structure and sequence. However, between human and bacterial Hsp70, there is approximately 50% of conservation. The idea that human Hsp70 and their bacterial counterparts have the same properties is not yet established. However, they do have in common an atpasic N-terminal domain and a C-terminal domain that is able to bind to peptides. This is a relevant distinction between the present invention and the patent and non-patent references that circumscribe the topic.

The HspBP1 protein is deemed to be a member of a family of proteins present in eukaryotic cells, identified as HSP 70 nucleotide exchange factors, acts as co-chaperone, which exhibit varying degrees of enclosure and a specificity of the species. The HspBP1 protein is located mainly in the cytoplasm and in the nucleus, but can also be found outside the cell. Said protein, mostly expressed in the heart and skeletal muscle, is capable of binding to Hsp70 protein, inhibiting its activity and promoting dissociation of nucleotides within the ATPase domain. In addition, the HspBP1 protein inhibits the activity of HspA1A chaperone, changing the conformation of the ATP binding domain of HspA1A and obstructing the ATP bond. The HspBP1 protein has a role in the modulation of chaperones located on the surface of tumor cells.

There are Hsps that are constitutively produced and Hsps induced under stress. The main function of constitutive Hsps is probably acting as chaperone for proteins nascent during protein synthesis, having the function of, through the recognition and connection to these polypeptides, promoting and ensuring its correct folding, which is essential for its correct operation. Subsequent studies verified an interaction between Hsp70 and HspBP1, showing that HspBP1 binds to Hsp70, modulating it. In such case, Hsp70 assumes the role as chaperone and HspBP1 as co-chaperone, i.e., binds to the chaperone, modulating it.

The function of induced Hsps seems to be central to the maintenance of cellular homeostasis, by binding themselves to total or partially denatured proteins, helping them to recover their original tertiary structure.

The patent literature and other documents from the prior art also portray studies involving HspBP1 protein.

Patent application WO 2001/81545 shows a method for the modulation of the expression of extracellular genetic material through the use of HspBP1 polypeptides and polynucleotides. The present invention differs from the above document because, among other technical reasons, unlike the present invention, it does not describe a method of genetic material expression modulation through the modulating activities of protein HspBP1. Nor the use of HspBP1 protein non-natural fragment(s) for such applications is revealed or suggested.

The article "Increased Expression of Hsp70 Cochaperone HspBP1 in Tumors", published in Oct. 27, 2003 in Tumour Biology: the Journal of the International Society for Oncodevelopmental Biology and Medicine, reports the alteration of HspBP1 protein levels in murine tumors. Said Article provides that tumors in mouse have high levels of HspBP1 protein compared to normal tissues. This study also describes that the HspBP1 protein binds to and reduces the activity of the Hsp70 protein. The present invention differs from the above Article, because, among other technical reasons, it surprisingly lists the connection between HspBP1 to Hsp70 and reduction of tumor growth. With this, it suggests the direct administration of the HspBP1 protein for therapeutic purposes, which was not disclosed or even suggested in said Article. Nor the use of HspBP1 protein non-natural fragment(s) for such applications is revealed or suggested.

The article "HspBP1 levels are elevated in breast tumor tissue and inversely related to tumor aggressiveness", published in Nov. 6, 2008 in Cell Stress and Chaperones, discloses that HspBP1 protein is increased in tumor tissues in relation to the normal adjacent tissues. Said article also describes that the HspBP1 co-chaperone levels are inversely related to the aggressiveness of the tumor. The article does not anticipate or even suggest the object of the present invention, which is characterized by providing an anti-tumor therapeutic option through the direct administration of HspBP1 protein. Nor the use of HspBP1 protein non-natural fragment(s) for such applications is revealed or suggested.

The article "The Heat Shock-binding Protein (HspBP1) Protects Cells against the Cytotoxic Action of the Tag7-Hsp70 Complex", published on Mar. 25, 2011 in The Journal of biological chemistry, discloses the inhibitory effect of HspBP1 protein on the Hsp70-Tag7 complex cytotoxic activity (Tag7 being a peptidoglycan recognition protein PGRP-S), which form a cytotoxic complex against certain tumor cells. According to the article, such inhibitory effect can be a defense mechanism of normal cells of adjacent tissues against the cytotoxicity of said complex. The present invention differs from that document because, among other technical reasons, it describes the administration of HspBP1 protein in order to decrease tumor growth. Nor the use of HspBP1 protein non-natural fragment(s) for such applications is revealed or suggested.

The article "Heat shock protein 70-binding protein 1 is highly expressed in high-grade gliomas, interacts with multiple heat shock protein 70 family members, and specifically binds brain tumor cell surfaces", published on Jul. 30, 2009 in Cancer Science, considered the closest document in relation to the present invention, discloses that HspBP1 protein binds to the Hsp70 proteins located at the surface of tumor cells, internalizing itself therein and playing a role in chaperone modulation. The present invention differs substantially from said article because, among other differences, it proves that through the administration of HspBP1 protein, a tumor growth reduction is achieved. Nor the use of HspBP1 protein non-natural fragment(s) for such applications is revealed or suggested in such prior art.

The article by Tanimura et al. "Anticancer Drugs Upregulate HspBP1 and thereby antagonize the Prosurvival Function of Hsp70 in Tumor Cells" (*The Journal of Biological Chemistry* vol. 282, No. 49, pp. 35430-35439, Dec. 7, 2007) describes that the increased HspBP1 expression antagonizes the Hsp70 pro-survival effect, sensitizing tumor cells to cathepsin-mediated death. However, they have not demonstrated this action in B16F10 cells. Nor the use of HspBP1 protein non-natural fragment(s) for such applications is revealed or suggested.

In view of the documents listed above, it will be observed that in the literature, no documents were found relating the use of HspBP1 protein, or non-natural fragment(s) thereof, in the preparation of medicinal products for the reduction of tumor growth through direct administration, nor suggesting that their results would be surprisingly as better as they are in this invention.

Currently, the treatment regimens for patients with tumors are performed by combining different chemotherapeutic drugs, most of them having low specificity and high cytotoxicity. The chemotherapeutic drugs have their therapeutic action based essentially on injury to cell mitosis, effectively affecting fast growing cells. Therefore, they cause cell damage, being called cytotoxic or cytostatic. Some of these drugs cause apoptosis (programmed cell death), causing side effects in other rapid division cells of the body that are not necessarily linked to the disease, such as, for example, intestinal epithelium cells and cells responsible for hair growth.

Another disadvantage of the current chemotherapy therapeutic regimen is the fact that during the treatment period, neoplastic cells become resistant to current chemotherapeutic drugs. One recent aspect is the development of a mechanism of pumps that are located on the surface of cancerous cells, which active and continuously move chemotherapeutic agents out of the target cell. This fact is connected, mainly, to the P-glycoprotein, which currently has become an important target of studies.

HspBP1 and Hsp70 proteins can be secreted from tumor cells and it is well-established that Hsp70 is present in human serum. Among other results, the present inventors have demonstrated that patients with malignant breast tumors had twice the level of HspBP1 in their sera in comparison with the control patients and malignant breast tumors contained HspBP1 (and Hsp70) levels 4 times higher than in normal adjacent tissue. In these studies, it was also observed that the tumors having the lowest HspBP1 levels became metastatic and resulted in more deaths among the patients. A recent analysis showed that extracellular HspBP1 co-chaperone binds to the surface of tumor cells by binding to Hsp70 chaperone (which, in turn, can be found in the surface of tumor cells), causing tumor reduction effects. These results support the inventors' hypothesis that the HspBP1 co-chaperone protein, or non-natural fragment(s) thereof, reduces tumor growth through its binding to cell surface proteins of tumors.

The present invention differs and surpasses the current chemotherapy therapeutic regimen as it is proposed as a highly specific and negligibly cytotoxic alternative for tumor growth reduction, since it comprises a Hsp70 binding compound (protein which is present in the surface of tumor cells), negatively modulating it, which results in anti-tumor effect. In addition, because it is specific, the approach of the present invention does not have the disadvantages related to drugs currently used in the current chemotherapy therapeutic regimen.

BRIEF SUMMARY OF THE INVENTION

The present invention has as the inventive concept common to its various objects the use of HspBP1 protein, or non-natural fragments thereof, as Hsp70 binder. Among other advantages, the present invention provides substantial benefits over the known chemotherapeutic agents, notably regarding the mechanism by which tumors are fought, since the HspBP1 protein or the non-natural fragment(s) thereof do not show toxicity and specifically bind to another protein, the Hsp70, which is present in the surface of tumor cells, while keeping normal body cells intact. In addition, the Hsp70 binding compound of the present invention operates in the sensitization of tumor cells to death by oxidative stress and enhances the action of chemotherapeutic agents. The invention provides, in addition, a large anti-tumor potential, acting in different cell lines. The invention also provides a new experimental model in vivo and in vitro for the development/evaluation of anti-tumor agents.

It is an object of the present invention to provide a Hsp70 binding compound comprising at least one polypeptide having at least 90% similarity with HspBP1 (SEQ ID No: 1) or at least one polypeptide having at least 90% similarity with the sequence that consists of amino acids 1-136 of SEQ ID No: 1 or functional equivalent variations thereof. In an embodiment, the functional equivalent variations are fragments of the polypeptides which are effective in the binding to Hsp70, or combinations thereof. In an embodiment, said functional equivalent is a non-natural peptide corresponding to amino acids 1-136 of HspBP1.

It is another object of the present invention to provide the use of a Hsp70 binding compound as defined above for the preparation of an anti-tumor drug. In one embodiment, said compound is a non-natural peptide corresponding to amino acids 1-136 of HspBP1.

It is another object of the present invention to provide an anti-tumor pharmaceutical composition comprising a pharmaceutically acceptable carrier and at least a Hsp70 binding compound. In one embodiment, the pharmaceutical composition additionally comprises a chemotherapeutic agent selected from the group consisting of hydrogen peroxide, cisplatin, and combinations thereof. In another embodiment of the pharmaceutical composition, the pharmaceutically acceptable carrier is a carrier for intravenous administration.

It is yet another object of the present invention to provide a gene construct for the Hsp70 binder expression, said gene construct comprising at least one vector and/or plasmid comprising an encoding sequence that expresses a Hsp70 binding compound in prokaryotic or eukaryotic cells, such gene construct being especially useful in the treatment of tumors on mammals by gene therapy. In one embodiment, said encoding sequence encodes HspBP1 (SEQ ID No: 1) or a non-natural peptide corresponding to amino acids 1-136 of HspBP1.

It is yet another object of the present invention to provide a process for the production of anti-tumor pharmaceutical composition comprising the steps of:

(a) preparing an active ingredient comprising a Hsp70 binding compound; and (b) adding a pharmaceutically acceptable carrier.

In one embodiment, the process comprises additionally the incorporation of at least one other chemotherapeutic agent; and/or at least one fluorescent or radioactive compound; and/or at least one biodegradable polymer in the composition.

It is yet another object of the present invention to provide a method of sensitization of tumor cells to chemotherapeutic agents, comprising the exposure of tumor cells to a pharmaceutical composition comprising at least one polypeptide having at least 90% similarity with HspBP1 (SEQ ID No:1) or at least one polypeptide having at least 90% similarity with the sequence consisting of amino acids 1-136 of SEQ ID No: 1 or functional equivalent variations thereof. In one embodiment of said method of sensitization, the composition comprises the non-natural polypeptide corresponding to amino acids 1-136 of HspBP1. In one embodiment of the method of sensitization, the chemotherapeutic agent is selected from the group consisting of hydrogen peroxide, cisplatin or combinations thereof. In one embodiment of the method of sensitization, the tumor cells are melanoma and glioma cells.

It is yet another object of the present invention to provide a method of treatment of tumors comprising the administration to an individual of an anti-tumor pharmaceutical composition comprising:

(a) at least a Hsp70 binding compound; and (b) a pharmaceutically acceptable carrier.

In one embodiment, the method additionally comprises a step of heat shock. In one embodiment of the method of present invention, the administration occurs intratumorally, intravenously and/or parenterally in the individual.

These and other objects of this invention will be better understood and appreciated from the detailed description of the invention and the appended claims.

DETAILED DESCRIPTION OF PREFERRED EMBODIMENTS

Figures 1, 2:
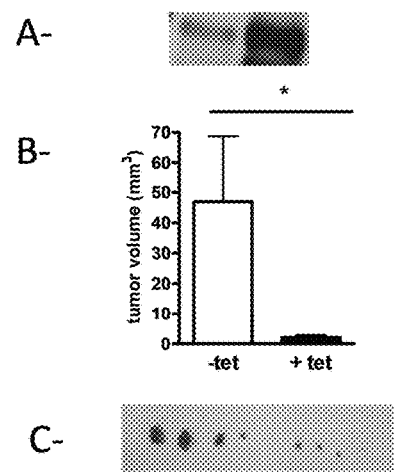
FIG. 1 shows an alignment between mice and human HspBP1 showing 94% identity.
FIG. 2 illustrates that the human HspBP1 overexpression inhibits human tumor growth in vivo.

The present invention has as the inventive concept common to its various objects the use of HspBP1 protein, or non-natural fragments thereof as Hsp70 binder. The objects of the invention include: a Hsp70 binding compound; the use of a Hsp70 binding compound for the preparation of an anti-tumor pharmaceutical composition; an anti-tumor pharmaceutical composition comprising a Hsp70 binding compound; a gene construct for the Hsp70 binder expression, said construct being particularly useful for gene therapy for the treatment of tumors in mammals; a process of production of said pharmaceutical composition; a process for the evaluation of potentially treatable tumor cells by contacting the tissue or tumor cells with the Hsp70 binding compound; and a method of sensitization of tumor cells to chemotherapeutic agents.

The following are some definitions of terms that are used throughout the patent application.

Similarity

In the context of this patent application, "having at least 90% similarity" should be understood as the fact of maintaining at least 90% identity with the peptide (SEQ ID NO: 1) or at least 90% similarity with the sequence composed of amino acids 1-136 of SEQ ID No: 1. The modifying of sequences having similar characteristics, e.g., hydrophobicity or hydrophilicity, in order to optimize their function or even for practical or economic purposes is known in the art.

Functional Equivalent Variation

In the context of the present invention, the term "functional equivalent variant" should be understood as any peptide that, irrespective of the amino acid chain size, possesses the same biological function and/or the same biological effect of the peptide sequences to which they relate. Such as, for example, segments or fragments of the amino acid chain to which they relate, including but not limited to the non-natural peptide corresponding to amino acids 1-136 of HspBP1.

B16F10 Cells

B16F10 cells are murine melanoma cells characterized by being more resistant to a given concentration of chemotherapy drugs, such as methotrexate or N-(phosphonacetyl)-L-aspartate and have an increased generation rate of metastatic variants, suggesting a gene amplification mechanism that may be involved in the expression of the metastatic phenotype.

Chemotherapeutic Agents

Chemotherapeutic agents, also called antineoplastic agents, are drugs that generally act harming cell mitosis of neoplastic cells or by inducing these neoplastic cells to apoptosis (programmed cell death). This means that they also damage the rapidly dividing cells under normal circumstances, such as cells from bone marrow, digestive tract and hair follicles.

It is important to note that some drugs, although commonly used in other types of treatment, such as antibiotics, hormone inhibitors/stimulators and monoclonal antibodies may be considered chemotherapeutic agents, as they have adjuvant roles in anti-tumor treatment.

The chemotherapeutic agents of the present invention may also be selected from the following groups:

TABLE 1

| | |
|---|---|
| Alkylating agents | Nitrogen mustards, Ethylenimines and Methylmelamines, Alkylsulfonates, Nitrosoureas, Triazenes, Platinum Complexes, among others. |
| Antimetabolites | Folic acid analogues, Purine analog, Pyrimidine analogs, among others. |
| Mitotic Inhibitors | Vinca alkaloids, Terpenoids, among others. |
| Antitumor antibiotics | Anthracyclines, Streptomycins, Hydroxyurea, among others. |
| Topoisomerase Inhibitors | Type I, Type II, among others. |
| Hormone therapy | Drugs which inhibit/stimulate appropriate changes in the hormonal balance (finasteride, aromatase inhibitors, tamoxifen, goserelin), steroids (dexamethasone), among others. |
| Monoclonal Antibodies | Adalimumab, Trastuzumab, Cetuximab and Rituximab, among others. |

Note: The chemotherapeutic agents mentioned in Table 1 above can be used in the pharmaceutical composition of the present invention alone (with the Hsp70 binding compound) or in combination with chemotherapeutic agents of the same therapeutic class or different classes.

The chemotherapeutic agents mentioned in Table 1 above are: alkylating agents (add alkyl grouping to electronegative groups of the cell DNA—being non-specific, because they attack both cancer cells and healthy cells, altering or preventing cell replication), antimetabolites (competes with the metabolite, as it has similar structure to the metabolite necessary for normal biochemical reactions, thus inhibiting the normal function of the cell), mitotic inhibitors (inhibit cell mitosis), anti-tumor antibiotics (antibiotics that possess cytotoxic activity), topoisomerase inhibitors (inhibit enzymes that act on DNA topology), hormone therapy (drugs that cause changes in hormonal balance can have an inhibitory effect on certain types of tumors) and monoclonal antibodies (main role of monoclonal antibodies is to simulate the patient's immune system to attack the malignant tumor cells and prevent their growth by blocking receptors specific to the cell).

Pharmaceutically Acceptable Carrier

In the context of the present invention, the "pharmaceutically acceptable carrier" should be understood as the excipients used in the pharmaceutical composition to provide the proper delivery of the active ingredient(s) to the subject.

The present invention is therefore related to a Hsp70 binding compound, the use of a Hsp70 binding compound for the preparation of an anti-tumor pharmaceutical composition; to an anti-tumor pharmaceutical composition comprising a Hsp70 binding compound, its production process, a method of evaluation of treatable tumors (companion test) by contacting the tissue or tumor cell with the Hsp70 binding compound; to a gene construct for expression of said compound; to a method of tumor sensitization; and to a method for tumor treatment using said composition.

The anti-tumor pharmaceutical composition of the invention comprises: a pharmaceutically acceptable carrier; and at least a Hsp70 binding compound comprising at least one polypeptide having at least 90% similarity to SEQ ID No: 1 or at least one polypeptide having at least 90% similarity with the sequence that consists of amino acids 1-136 of SEQ ID No: 1 or functional equivalent variations thereof. In one embodiment, the pharmaceutical composition of the invention comprises, as binder, a non-natural peptide corresponding to amino acids 1-136 of HspBP1. In one embodiment, the pharmaceutical composition of the invention additionally comprises: another chemotherapeutic agent selected from the group consisting of hydrogen peroxide, cisplatin or combinations thereof; and/or a fluorescent or radioactive compound and/or a biodegradable polymer.

The gene construct of the invention for the Hsp70 binder expression comprises: a sequence encoding a Hsp70 binding polypeptide, said polypeptide having at least 90% similarity to SEQ ID No: 1 or at least one polypeptide having at least 90% similarity with the sequence that consists of amino acids 1-136 of SEQ ID No: 1 or functional equivalent variations thereof; a promoter sequence operatively linked to said encoding sequence; said promoter and encoding sequences being present in a vector or functional plasmid for expression of said polypeptide in prokaryotic or eukaryotic cells. In one embodiment, the gene construct comprises the encoding sequence encoding the HspBP1 or non-natural peptide corresponding to amino acids 1-136 of HspBP1.

The process of producing an anti-tumor pharmaceutical composition of the invention comprises the steps of:—preparing an active ingredient comprising a Hsp70 binding compound comprising at least one polypeptide having at least 90% similarity with SEQ ID No: 1 or at least one polypeptide having at least 90% similarity with the sequence that consists of amino acids 1-136 of SEQ ID No: 1 or functional equivalent variations thereof; and adding a pharmaceutically acceptable carrier. In one embodiment, the process additionally comprises the incorporation of at least one chemotherapeutic agent; and/or at least one fluorescent or radioactive compound; and/or at least one biodegradable polymer in the composition.

The process for evaluating tumor cell of the invention comprises:—contacting tumor cells to a Hsp70 binder comprising at least one polypeptide having at least 90% similarity with SEQ ID No: 1 or at least one polypeptide having at least 90% similarity with the sequence that consists of amino acids 1-136 of SEQ ID No: 1 or functional equivalent variations thereof; and the Hsp70 binder binding identification and/or its effects.

The method of sensitizing tumor cells to chemotherapeutic agents of the invention comprises contacting tumor cells with a polypeptide having at least 90% similarity to SEQ ID No: 1 or at least one polypeptide having at least 90% similarity with the sequence consisting of amino acids 1-136 of SEQ ID No: 1 or functional equivalent variations thereof.

One of the novel aspects of the present invention is the high specificity with respect to that obtained by currently used chemotherapeutic agents, acting directly on the neoplastic cells.

Another novel aspect is the mechanism by which the protein inhibits the increase of the tumor and also contributes to tumor shrinkage, which occurs through the binding between the HspBP1 co-chaperone, or non-natural fragments thereof, to the Hsp70 chaperone present on the surface of tumor cells. This binding results in a down modulation of the chaperone which, in turn, has an anti-tumor action. The use of HspBP1 protein, or non-natural fragments thereof, as an adjuvant in anti-tumor treatment may abolish or diminish the amounts usually used of chemotherapeutic agents, consequently reducing the side effects associated with these drugs. It was also found that the Hsp70 binding compound acts as a tumor cell sensitizer to chemotherapeutic agents by increasing the effect of killing tumor cells by the application of chemotherapy agents.

The tumor cell death by oxidative stress can be induced, e.g., with the addition of hydrogen peroxide. Since the Hsp70 protein also protects the tumor cells against induced death by oxidative stress, the administration of the Hsp70 binding compound to a subject having cancer sensitizes tumor cells to death by oxidative stress. Thus, the effectiveness of cancer treatment with oxidizing compounds such as, for example, hydrogen peroxide, is increased by administration of the Hsp70 binding compound.

Additionally, it was reported that HspBP1 might enhance the effect of chemotherapeutic agents already used in clinical practice. From the results, it was possible to observe that the administration of HspBP1 enhances the effect of tumor cell death by action of chemotherapy agents (e.g. cisplatin) acting as a chemo-sensitizer.

A relevant and surprisingly revealed fact is the high degree of analogy between human HspBP1 protein and murine HspBP1 protein. The mouse and human forms of the proteins are 94% similar in relation to the amino acid sequence as described in FIG. 1.

For the HspBP1/Hsp70 molar ratio, the patients were categorized into groups having molar ratios that were equal or above 4.0. This is the value that, according to Raynes et al. (2003), results in 50% inhibition of Hsp70 ATPase activity.

The present inventors sought to develop a new tumor treatment based on the binding of HspBP1 co-chaperone (Hsp70 binder) to Hsp70.

HspBP1 binds to another protein, the Hsp70 (which is present in the outer surface of most tumor cells, modulating it negatively. Results of tests performed by the inventors suggest that HspBP1 is a multifunctional protein. Inside the cell, it modules the activity of the Hsp70, while outside the cell, the HspBP1 binds to Hsp70 and inhibits tumor growth. Extracellular HspBP1 can be found in human blood. However, it was surprisingly observed that, when circulating levels of HspBP1 were artificially increased through intravenous injections in tumor bearing mice, the tumor growth was reduced. Therefore, it was concluded and verified that the negative modulation which the HspBP1 produces through binding to the Hsp70 has anti-tumor activity. The invention therefore additionally provides a new in vivo experimental model for the development of new anti-tumor agents.

The present inventors have also identified and described the Hsp70 binding compound (HspBP1) active segment that has anti-tumor activity, see SEQ. ID No: 1.

In one embodiment of the invention, the Hsp70 binding compound of the present invention comprises at least one polypeptide having at least 94% similarity with SEQ ID No: 1. In another embodiment, the Hsp70 binding compound comprises at least one polypeptide having at least 99% similarity with SEQ ID No: 1.

In one additional embodiment of the invention, the Hsp70 binding compound comprises at least one polypeptide having at least 90% similarity with the sequence that consists of amino acids 1-136 of SEQ ID No: 1. In another embodiment, the Hsp70 binding compound comprises at least one polypeptide having at least 99% similarity with the sequence that consists of amino acids 1-136 of SEQ ID No: 1.

Additionally, it was found that in vivo overexpression of HspBP1 acts in synergy with the individual's immune system. The tests suggest that tumor size regression by administering the Hsp70 binding compound in immunodeficient individuals was lower than regression in normal individuals.

All findings presented herein suggest that this protein has anti-tumor potential. From this evidence, it several tests were performed, including intravenous injection of HspBP1 protein.

The following examples illustrate several of such procedures in order to assist in understanding the scope of the invention and its advantages. The following details and reported cases aim to facilitate the reproduction of the invention, and should therefore be construed as merely illustrative, without thereby restricting the scope of the invention.

The experiments presented below were performed using murine and human HspBP1. In one embodiment, the present invention proposes the development of a treatment for cancer in humans. Therefore, it is important to document the degree of identity between human and mouse forms of HspBP1 protein, as can be seen in FIG. 1. The mouse and human forms of the protein are 94% identical in relation to the amino acid sequence. The protein sequence is filed in the Gene Bank (Gene ID: 23640).

Evidence 1—The Increased Expression of HspBP1 and Truncated HspBP1 within the Tumor Cells Reduces In Vivo Tumor Growth As part of the experimental strategy, a gene construct was designed and implemented for the Hsp70 binder expression, said construct being particularly useful for gene therapy for the treatment of mammalian tumors. Said gene construct comprises:

a sequence encoding a Hsp70 binding polypeptide;
a promoter sequence operatively linked to said encoding sequence;
said promoter and coding sequences being present on a vector or functional plasmid for expression of said polypeptide in prokaryotic or eukaryotic cells. In this context, a system was developed in which HspBP1 expression was regulated by the presence of tetracycline. B16F10 cells were stably transfected with pcDNA6/TR plasmid, the transfected clones were selected using antibiotic and then the cells were transfected with a plasmid containing the sequence encoding human HspBP1, or empty vector as a control. The HspBP1 increased expression was verified by adding tetracycline to the culture medium. The transfected cells were injected subcutaneously into the thigh of mice; one group of mice received tetracycline in drinking water and the other did not. Tumor growth was clearly reduced in the group of mice with induced human HspBP1 overexpression. The average tumor volume with increased HspBP1 expression was 2.07 mm$^3$, while the average tumor volume of control tumors was 46.9 mm$^3$ (FIG. 2).

The B16F10 cells were stably transfected with pcDNA6/TR and pcDNA4/TO plasmids with or without the human HspBP1 sequence. A)—Western blot analysis demonstrating HspBP1 overexpression after induction with tetracycline for 24 hours in vitro, left uninduced BP1, right induced BP1. B)—The stably transfected cells ($5 \times 10^5$) were injected subcutaneously into the thigh of mice and Tetracycline (1 ug/ml) was added to drinking water to induce HspBP1 expression. Tumors of mice which either received or did not receive tetracycline were collected and the tumor volume was measured. C)—Photograph of tumors removed from mice that received (right) or did not receive (left) tetracycline. Quantification of tumor growth inhibition by HspBP1 (Mann-Whitney test, /d/p<0.05). Tumor volume (V) was calculated using V=d2×D×0.5, where d=smaller diameter and D=larger diameter.

Figure 3:
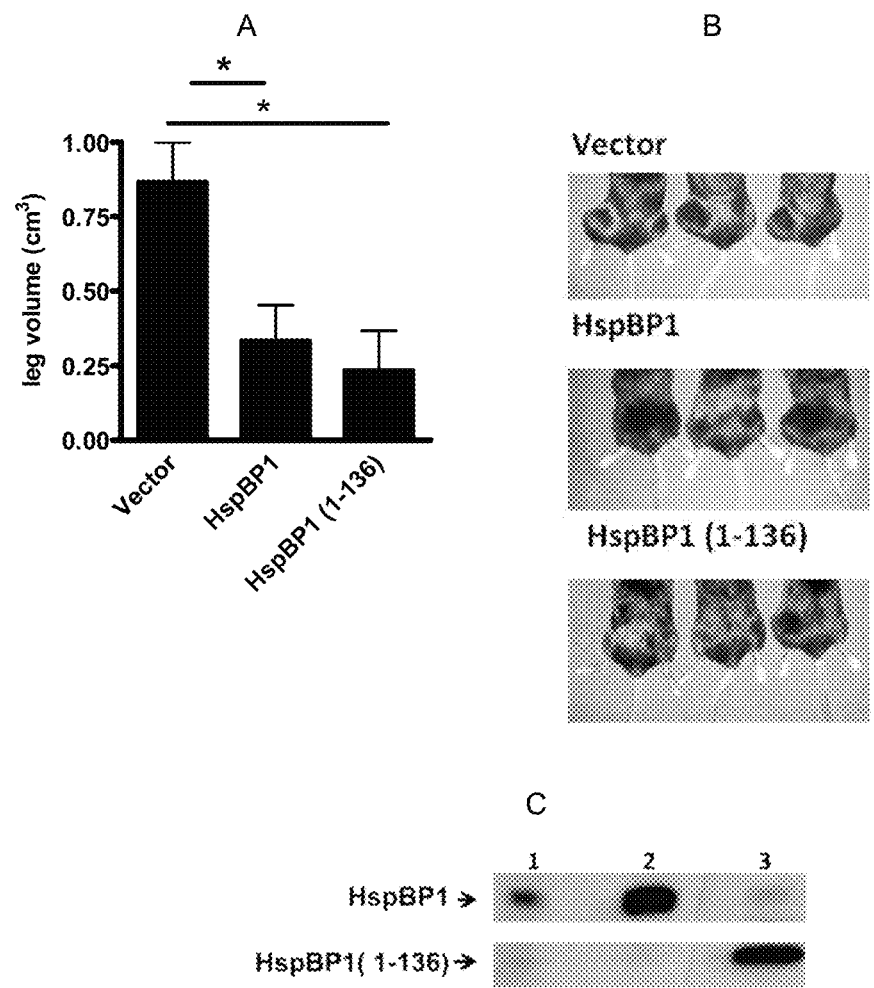
FIG. 3 illustrates murine HspBP1 and HspBP1 (1-136) overexpression inhibits tumor growth in vivo.

Working with the possibility that human HspBP1 protein is recognized by the mouse immune system and that this is the reason for the tumor growth reduction, we decided to repeat the experiments using murine HspBP1. The B16F10 cells were transiently transfected with plasmid containing the sequence encoding the murine HspBP1 or seed vector as a control, and these cells were injected subcutaneously in the mouse thigh. Tumor growth was monitored for 20 days by measuring the volume of the thigh using a digital caliper. The results demonstrate that murine HspBP1 expression inhibits tumor growth. In addition, a non-natural version of the HspBP1 peptide (such as, for example, a fragment having amino acids 1-136) referred to as truncated HspBP1 also inhibits tumor growth, showing that the entire protein is not required for the therapeutic effect to take place (FIG. 3).

B16F10 cells ($5 \times 10^5$) were transiently transfected with pcDNA4/TO plasmid alone or containing the sequence encoding HspBP1 and HspBP1 (1-136) protein and, after 24 h, were injected subcutaneously into mice. A)—Quantification of tumor growth inhibition by HspBP1 after 20 days of tumor growth (Mann-Whitney test, p<0.05). B)—Tumor-bearing mice were photographed after 20 days of tumor growth. C)—Western blot analysis showing in vitro HspBP1 and truncated HspBP1 (1-136) expression on transfected cells.

Figure 4:
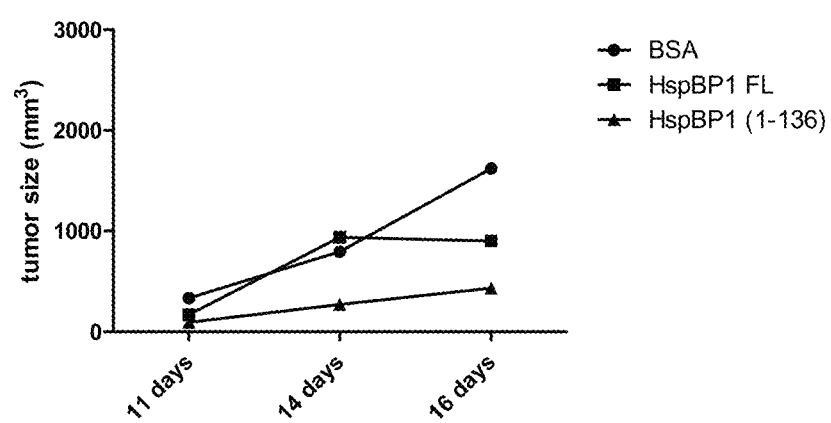
FIG. 4 illustrates the effect of HspBP1 and HspBP1 (1-136) intratumoral injection in tumor growth inhibition.

Evidence 2—Treatment with HspBP1 and Truncated Extracellular HspBP1 Reduces Tumor Growth The recombinant form of the non-natural 1-136 peptide was produced. Then melanoma-bearing mice were treated with whole protein (FL) or only with said peptide. The results indicate that the latter was even more effective in reducing tumor. As can be seen in FIG. 4, $4 \times 10^5$ B16F10 cells were injected subcutaneously into mice at their thighs. 3 and 6 days later, 40 ug HspBP1, BSA or truncated HspBP1 were intratumorally injected in 100 uL PBS. Tumor growth was monitored for 16 days. Tumor sizes were measured using a caliper. Tumor volume (V) (mm3) was calculated using V=d2×D×0.5, wherein d=smaller diameter and D=larger diameter.

Furthermore, it was shown that truncated HspBP1 inhibits tumor growth by inducing apoptosis in vivo. We performed ex vivo tests to verify that HspBP1 treatment could activate caspase 3 in melanoma. $8 \times 10^5$ cells/animals were injected and after 3 days they were treated with HspBP1 FL, HspBP1 (1-136) or OVA. After 24 hours, the tumor was removed and analyzed for activated caspase 3 by Western blot (FIG. 5).

Figure 5:
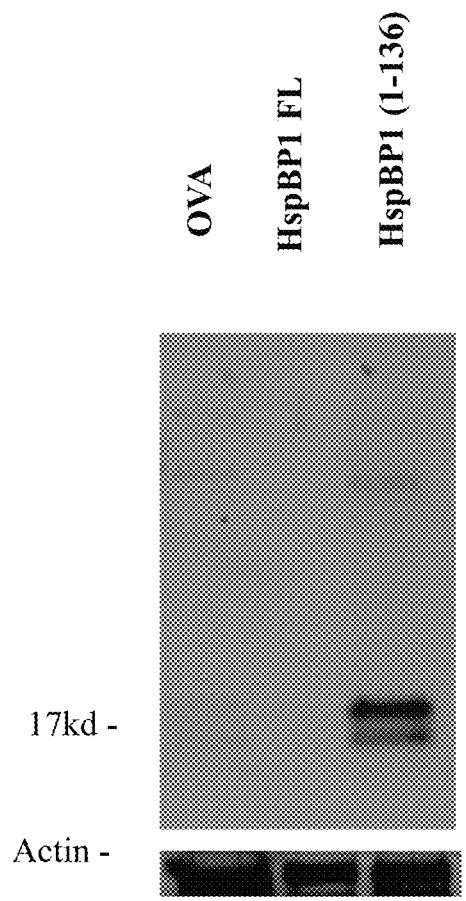
FIG. 5 shows the marking of activated caspase 3 and actin in ex vivo tumor samples treated with HspBP1 FL, truncated HspBP1 and OVA as a control. The 17 KDa band represents the marking of activated caspase 3.

As can be seen in FIG. 5, Western blot demonstrating the marking of activated caspase-3 and actin in ex vivo tumor samples treated with HspBP1 FL, truncated HspBP1 and OVA as a control. The 17 kDa band represents the marking of activated caspase 3.

Evidence 3—HspBP1 Binds to Hsp70 on the Surface of Tumor Cells

Studies have shown that Hsp70 and HspBP1 can be secreted by tumor cells (Evdonin et al., 2009) and it is well established that Hsp70 is present in human serum (Pockley et al., 1998). Our laboratory has shown that breast cancer patients had twice the HspBP1 level in their serum compared to tumor-free individuals. Furthermore, breast tumors contained HspBP1 (and Hsp70) levels that were 4 times higher than the normal adjacent tissue (Souza et al., 2009). It was also noted in this study that tumors having the lowest HspBP1 levels become metastatic and resulted in more deaths among patients. Recent analysis presented herein shows that HspBP1 and HspBP1 (1-136) can bind to the extracellular surface of tumor cells through the Hsp70 on the surface of the cells. These results support the hypothesis that HspBP1 reduces tumor growth by binding to the cell surface of tumor cells.

Figure 6:
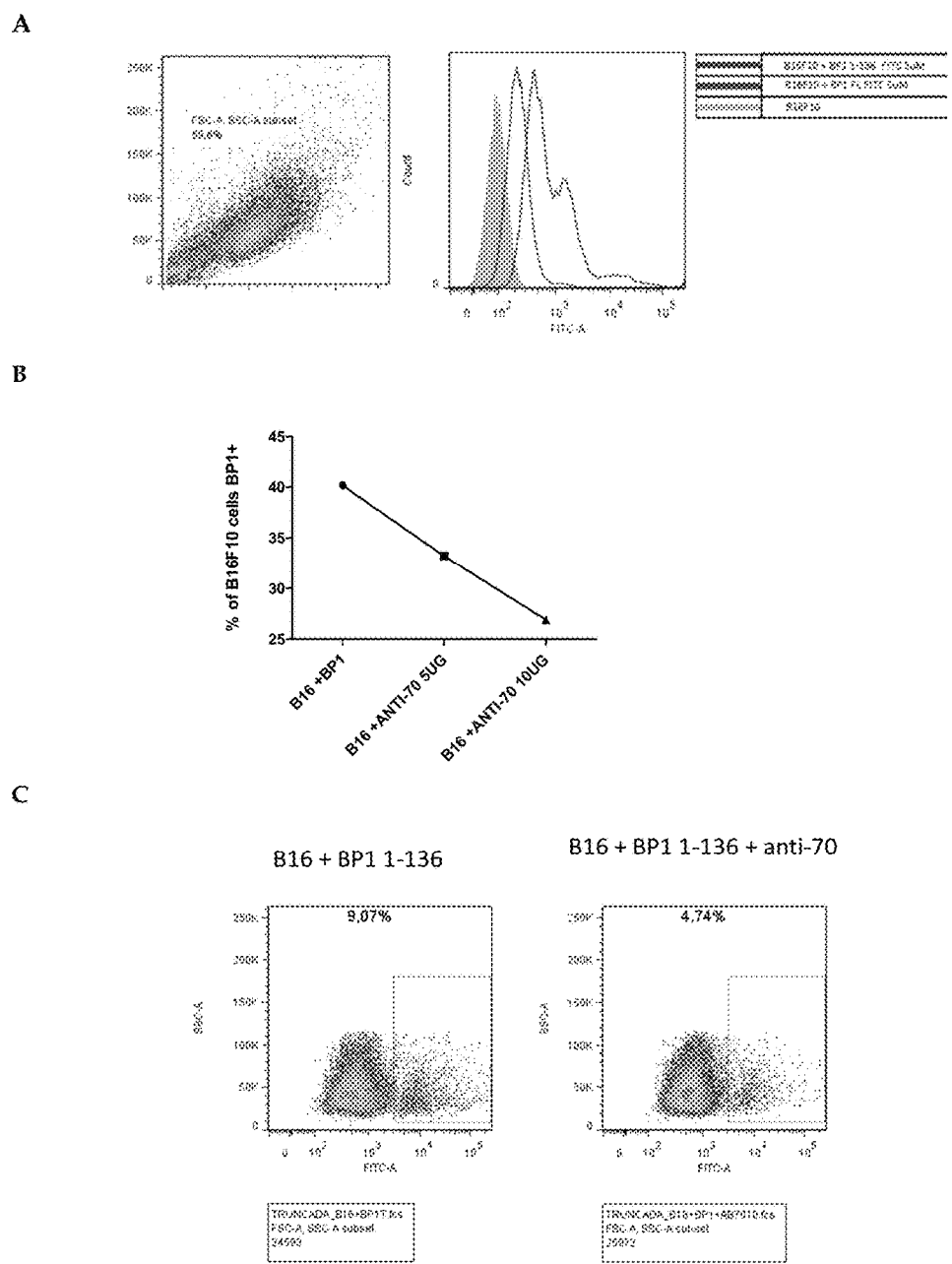
FIG. 6 illustrates the binding of HspBP1 in B16F10 cells analyzed by flow cytometry.

As can be seen in FIG. 6, the B16F10 Cells were incubated with 2.4G2 cell supernatant for 20 min. Fc receptors were blocked using B16F10 ($2 \times 10^5$) on the cells, then the cells were labeled for 2 hours on ice with HspBP1 (FL) or HspBP1 (1-136). Cells were acquired on FACS Canto II cytometer (BD bioscience), and the data were analyzed using the FlowJo software (TreeStar).

Such data suggests that HspBP1 is a multifunctional protein. Inside the cell, it regulates the Hsp70 activity while outside the cell, it binds to Hsp70 on the surface of the cells and inhibits tumor growth.

When Hsp70 is silenced in B16F10 cells using siRNA and when we submit the cells to heat shock, there is a reduction in the number of viable cells in vitro (FIG. 3). However, when we over-express HspBP1 and HspBP1 (1-136) and we submit these cells to heat shock, no changes occur in vitro.

Figure 7:
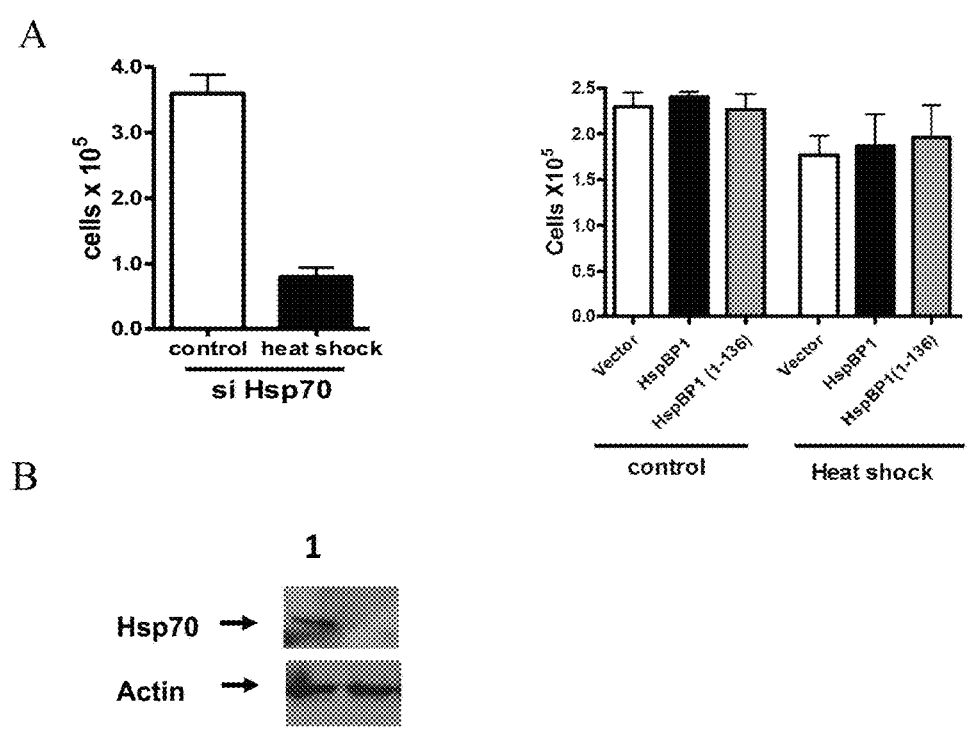
FIG. 7 illustrates cell survival after heat shock.

As can be seen in FIG. 7, A—Analysis of in vitro viability of B16F10 cells, after silencing Hsp70 with siRNA, with or without heat shock. B—Western blot analysis of Hsp70 and actin expression in B16F10 cells, after silencing Hsp70 with siRNA. Cells were treated with control siRNA (lane 1) or Hsp70 siRNA (lane 2) and subsequently heat shocked at 42° C. for 2 hours, followed by a recovery of 37° C. for 4 h. C—Survival of B16F10 cells transiently transfected with pcDNA4/TO plasmid containing the murine HspBP1 sequence or pcDNA4/TO plasmid having murine HspBP1 (1-136) sequence; with or without heat shock at 42° C. for 1 h.

During the course of tumor growth in vivo, Hsp70 and HspBP1 expression are inversely related as shown in FIG. 7. This may suggest a tumor cell control to confer survival associated with Hsp70 and HspBP1 expression.

Figure 8:
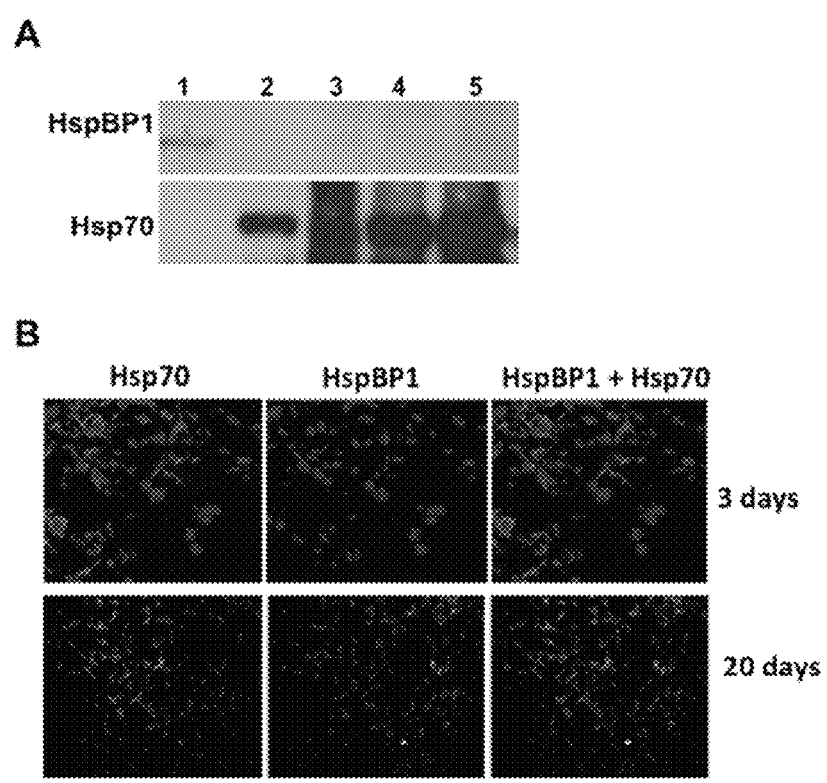
FIG. 8 illustrates in vitro and in vivo Hsp70 and HspBP1 expression in B16F10 melanoma cells.

FIG. 8 illustrates a Western blot analysis of Hsp70 and HspBP1 expression in vitro in B16F10 cells (lane 1) and different tumor growth stages in vivo. $5 \times 10^5$ B16F10 cells were injected subcutaneously into mice. Mice were sacrificed on days 3, 9, 15 and 20, and the tumors were removed for analysis. (b) Immunohistochemistry of tumor sections from days 3 and 20 of tumor growth. In blue are nuclei (stained with Hoechst), Hsp70 marking in red, and HspBP1 marking in green.

Evidence 4—HspBP1 and Truncated HspBP1 Chemo-sensitizer Effect

Figure 9:
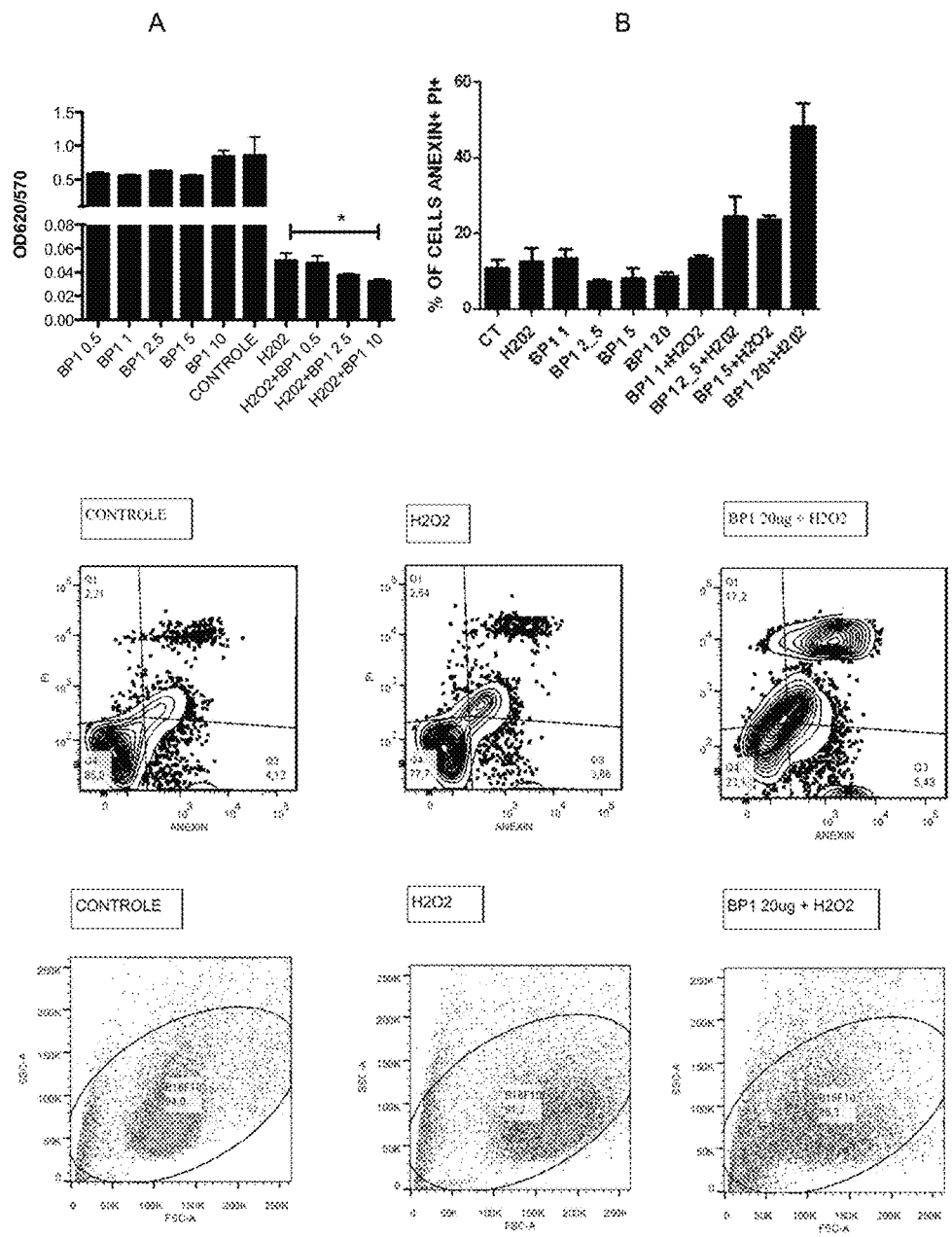
FIG. 9 illustrates that the addition of HspBP1 potentiates death induced by oxidative stress.

Since Hsp70 protects against death induced by oxidative stress—such as, for example, that induced in the treatment with hydrogen peroxide, we hypothesized that HspBP1 will sensitize tumors to death by oxidative stress, thereby enabling a tumor cell sensitization method to chemotherapeutic agents. HspBP1 was added at different concentrations with B16F10 cells cultured for 2h and then hydrogen peroxide was added. After 24 h and 12 h viability was assessed using MTT or by annexin and propidium iodide labeling to assess apoptotic cells. The addition of HspBP1 enhances death induced by oxidative stress, as can be seen in FIG. 9. As can be seen in FIG. 9, HspBP1 was added at different concentrations with B16F10 cells cultured for 2 h and then hydrogen peroxide was added. Viability was assessed using MTT after 24 hours (A) or by annexin and propidium iodide labeling after 12 h (B).

Figure 10:
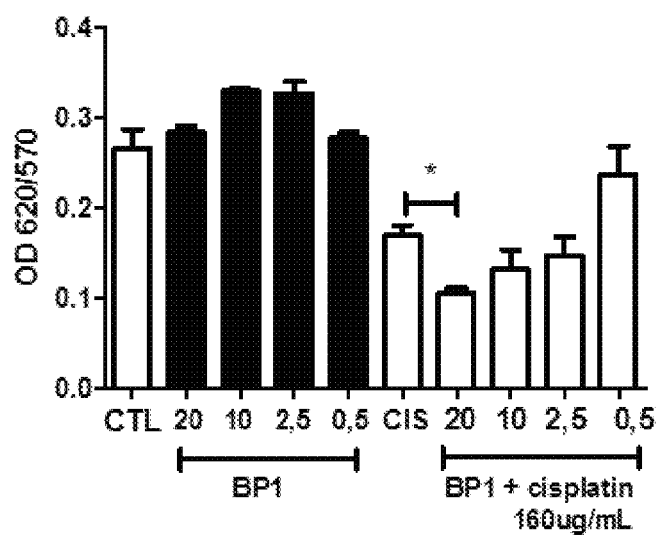
FIG. 10 illustrates the chemo-sensitizer effect of HspBP1.

It was also assessed whether HspBP1 may enhance the effect of chemotherapeutic agents already used in clinical practice. The B16F10 cells were plated at a concentration of $4 \times 10^3$ cells per well in a 96 well plate in 200 ul 10% DMEM medium. After 24 h, HspBP1 was added at different concentrations in AIM-V medium, and cells were incubated for 2 h; then cisplatin was added at a concentration of 160 ug/ml. After 14 h cell viability was assessed using MTT. We observed that HspBP1 enhances the effect of cisplatin death by acting as a chemo-sensitizer, as can be seen in FIG. 10.

The B16F10 cells were plated at a concentration of $4 \times 10^3$ cells per well in a 96 well plate in 200 ul 10% DMEM medium. After 24 h, HspBP1 was added at different concentrations in AIM-V medium, and cells were incubated for 2 h; then cisplatin was added at a concentration of 160 ug/ml. After 14 h, cell viability was assessed using MTT.

Evidence 5—Relationship of HspBP1 Effect with the Immune System

The lack of an anti-tumor effect of single HspBP1 treatment on B16F10 cells in culture and the reduction in tumor growth only in vivo suggests an interaction between tumor and host. One possibility is that the host immune system plays a role in in vivo tumor growth inhibition mediated by HspBP1. A comparison between wild WT mice (C57BL6/c) and immunodeficient mice (RAG–/–) was used to further explore the involvement of the immune system in tumor regression mediated by HspBP1 overexpression in B16F10 cells (FIG. 10). In WT mice, tumors transfected to overexpress HspBP1 were once again significantly smaller than tumors transfected only with the vector as a control. Tumors expressing HspBP1 were significantly smaller in WT than in RAG –/– mice, suggesting that adaptive immune response is involved in tumor growth inhibition by HspBP1. Finally, in RAG –/– mice, tumors expressing HspBP1 have a tendency to be smaller than tumors transfected with vector alone, although the difference was not significant.

Figure 11:
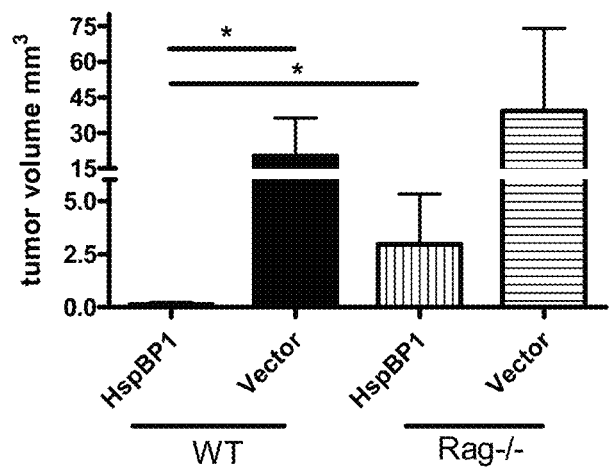
FIG. 11 illustrates the tumor growth that super-expresses murine HspBP1 in immunodeficient and wild mice.

As can be seen in FIG. 11, B16F10 cells transiently transfected with pcDNA4/TO plasmid containing the sequence encoding murine HspBP1 were injected into C57BL6/c WT and Rag –/– mice. Tumor volume (mm3) was measured after 25 days of tumor growth (Mann-Whitney test, p <0.05).

Figure 12:
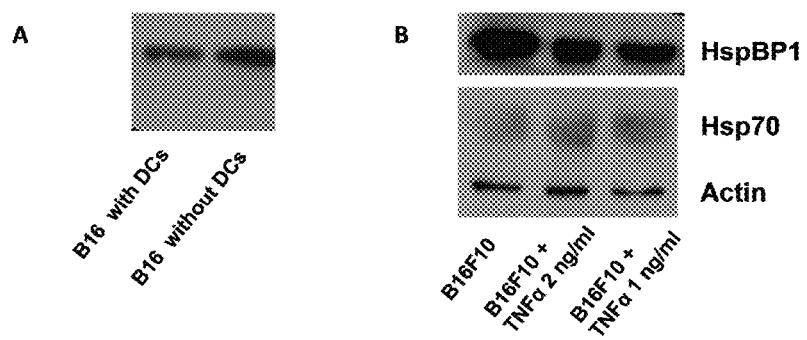
FIG. 12 illustrates an analysis of HspBP1 and Hsp70 expression in B16F10 cells by western blot.

To investigate whether tumor growth inhibition mediated by HspBP1 was associated with modulation of the innate immune response, in vitro and in vivo tests were performed. One of the first in vivo immune responses faced by tumor cells is the encounter with macrophages or dendritic cells and/or TNF-α production by these and other immune system cells. To test this hypothesis, we co-cultivated B16F10 cells with differentiated dendritic cells from bone marrow precursors (BMDC). Alternatively, we incubated B16F10 cells with different TNF-α concentrations. The results shown in FIG. 12, A and B indicate that these stimuli induce only a slight effect on HspBP1 (decreasing it to about 2 times) or Hsp70 (wherein a slight upregulation was observed) expression. This suggests that some modulation of the expression of both proteins can be performed by these innate response elements. According to FIG. 12, A-HspBP1 expression in B16F10 cells after 24h co-culture with differentiated dendritic cells from bone marrow precursors. B—HspBP1, Hsp70 and actin expression in B16F10 cells after stimulation with different TNF-αconcentrations for 48 hours.

Figure 13:
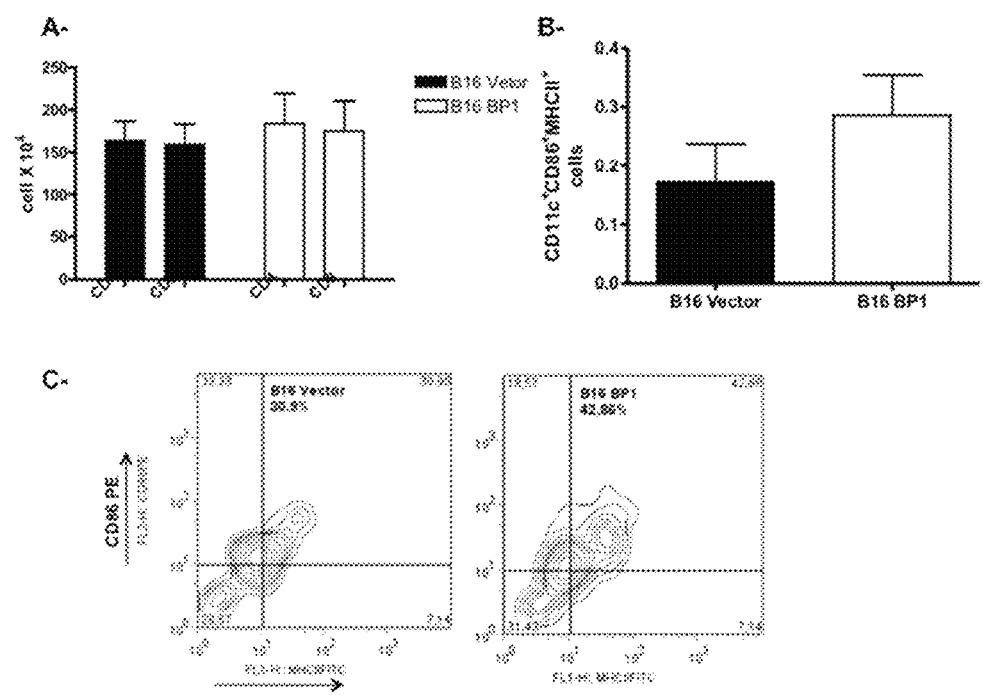
FIG. 13 illustrates a draining lymph node analysis of the tumor over-expressing HspBP1.

Furthermore, activation of dendritic cells and the number of CD4 and CD8 T cells in draining lymph nodes of tumor-bearing mice transiently over-expressing HspBP1 was evaluated. There was no difference in T cell frequency in the draining lymph nodes (FIG. 13A). However, we can notice a trend in the activation of dendritic cells in the lymph node of the tumor that expresses the most HspBP1. As can be seen in FIG. 13, $10^5$ B16F10 Cells transfected with the plasmid containing the sequence encoding murine HspBP1 or with vector alone were injected into the thigh of C57Bl6/c mice and after 25 days of tumor growth draining lymph nodes were excised, macerated to obtain a cell suspension and the cells were labeled with specific antibodies and analyzed by flow cytometry. A—Number of CD4+ or CD8+ T cells in draining lymph nodes. B—Number of CD11c+CD86+MHCII+ cells. C—Dot plot graph showing the frequency of CD11c+, CD86 +MHC-II+ dendritic cells.

Evidence 6—HspBP1 Antitumor Effect Occurs in Other Cell Lines In Vitro

Figure 14:
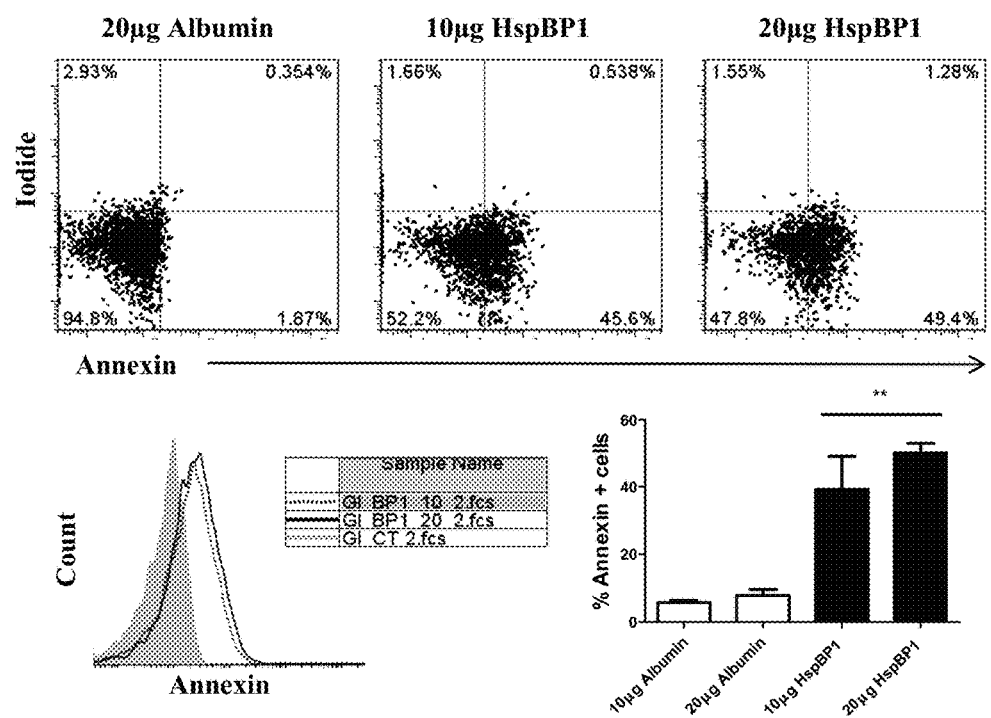
FIG. 14 shows marked glioma cells and illustrates the increase in the frequency of apoptotic cells when treated with HspBP1.

In vitro assays were performed to verify whether HspBP1 could induce cell death in GL, glioma cell line. $5 \times 10^5$ cells were seeded per well in a 24 well plate. Then, cells were incubated with 10 or 20 ug HspBP1 or albumin for 24 hours in DMEM containing 1% fetal bovine serum. After 24 hours, the samples were analyzed by flow cytometry using the Annexin V/iodide kit (BD). In FIG. 14, the labeled glioma cells are shown and we can see an increase in the frequency of apoptotic cells when treated with HspBP1. These data suggest that HsBP1 can function as an antitumor drug in more than one type of tumor.

Those skilled in the art will readily will appreciate the important benefits from the use of the present invention, being able, from the present description, to prepare drugs for tumor reduction. Variations in the ways of realizing the inventive concept exemplified herein shall be understood as within the spirit of the invention and the appended claims.

The invention claimed is:

1. An anti-tumor pharmaceutical composition for extracellular administration comprising:
   pharmaceutically acceptable carrier;
   at least one polypeptide consisting of SEQ ID No: 1; and
   cisplatin.

2. The composition according to claim 1, wherein the pharmaceutically acceptable carrier is, a carrier for intravenous administration.

3. The composition according to claim 1, wherein the composition is used for sensitization of tumor cells to chemotherapeutic agents.

* * * * *

UNITED STATES PATENT AND TRADEMARK OFFICE
CERTIFICATE OF CORRECTION

Page 1 of 1

PATENT NO. : 10,508,139 B2
APPLICATION NO. : 14/655608
DATED : December 17, 2019
INVENTOR(S) : Cazabuena Bonorino et al.

It is certified that error appears in the above-identified patent and that said Letters Patent is hereby corrected as shown below:

On the Title Page

Item (30) Foreign Application Priority Data, Column 1:
Please correct "102012033804" to read -- 102012033804-1 --

Item (56) References Cited, OTHER PUBLICATIONS, Column 2, Mazunnder et al. cite:
Please correct "Mazunnder" to read -- Mazumder --

In the Claims

Column 20, Line 32, Claim 2:
Please correct "carrier is, a" to read -- carrier is a --

Signed and Sealed this
Seventh Day of April, 2020

Andrei Iancu
*Director of the United States Patent and Trademark Office*

SEQUENCE LISTING

<160> NUMBER OF SEQ ID NOS: 3

<210> SEQ ID NO 1
<211> LENGTH: 136
<212> TYPE: PRT
<213> ORGANISM: Mus musculus

<400> SEQUENCE: 1

Met Ala Asp Lys Gly Ser Gly Gly Ser Arg Leu Pro Leu Ala Leu Pro
1               5                   10                  15

Pro Ala Ser Gln Gly Cys Ser Ser Gly Gly Ser Gly Ser Ser Ala Gly
            20                  25                  30

Gly Ser Gly Asn Pro Arg Pro Pro Arg Asn Leu Gln Gly Leu Leu Gln
        35                  40                  45

Met Ala Ile Thr Ala Gly Ser Gln Glu Pro Asp Pro Pro Glu Pro
    50                  55                  60

Met Ser Glu Glu Arg Arg Gln Trp Leu Gln Glu Ala Met Ser Ala Ala
65                  70                  75                  80

Phe Arg Gly Gln Arg Glu Glu Val Glu Gln Met Lys Asn Cys Leu Arg
                85                  90                  95

Val Leu Ser Gln Ala Thr Pro Ala Met Ala Gly Glu Ala Glu Leu Ala
            100                 105                 110

Thr Asp Gln Gln Glu Arg Glu Gly Ala Leu Glu Leu Leu Ala Asp Leu
        115                 120                 125

Cys Glu Asn Met Asp Asn Ala Ala
    130                 135

<210> SEQ ID NO 2
<211> LENGTH: 357
<212> TYPE: PRT
<213> ORGANISM: Mus musculus

<400> SEQUENCE: 2

Met Ala Asp Lys Gly Ser Gly Gly Ser Arg Leu Pro Leu Ala Leu Pro
1               5                   10                  15

Pro Ala Ser Gln Gly Cys Ser Ser Gly Gly Ser Gly Ser Ser Ala Gly
            20                  25                  30

Gly Ser Gly Asn Pro Arg Pro Pro Arg Asn Leu Gln Gly Leu Leu Gln
        35                  40                  45

Met Ala Ile Thr Ala Gly Ser Gln Glu Pro Asp Pro Pro Glu Pro
    50                  55                  60

Met Ser Glu Glu Arg Arg Gln Trp Leu Gln Glu Ala Met Ser Ala Ala
65                  70                  75                  80

Phe Arg Gly Gln Arg Glu Glu Val Glu Gln Met Lys Asn Cys Leu Arg
                85                  90                  95

Val Leu Ser Gln Ala Thr Pro Ala Met Ala Gly Glu Ala Glu Leu Ala
            100                 105                 110

Thr Asp Gln Gln Glu Arg Glu Gly Ala Leu Glu Leu Leu Ala Asp Leu
        115                 120                 125

Cys Glu Asn Met Asp Asn Ala Ala Asp Phe Cys Gln Leu Ser Gly Met
    130                 135                 140

His Leu Leu Val Gly Arg Tyr Leu Glu Ala Gly Ala Ala Gly Leu Arg
145                 150                 155                 160

Trp Arg Ala Ala Gln Leu Ile Gly Thr Cys Ser Gln Asn Val Ala Ala
                165                 170                 175

Ile Gln Glu Gln Val Leu Gly Leu Gly Ala Leu Arg Lys Leu Leu Arg

```
            180                 185                 190
Leu Leu Asp Arg Asp Ser Cys Asp Thr Val Arg Val Lys Ala Leu Phe
            195                 200                 205

Ala Ile Ser Cys Leu Val Arg Glu Gln Glu Ala Gly Leu Leu Gln Phe
        210                 215                 220

Leu Arg Leu Asp Gly Phe Ser Val Leu Met Arg Ala Met Gln Gln Gln
225                 230                 235                 240

Val Gln Lys Leu Lys Val Lys Ser Ala Phe Leu Leu Gln Asn Leu Leu
                245                 250                 255

Val Gly His Pro Glu His Lys Gly Thr Leu Cys Ser Met Gly Met Val
            260                 265                 270

Gln Gln Leu Val Ala Leu Val Arg Thr Glu His Ser Pro Phe His Glu
        275                 280                 285

His Val Leu Gly Ala Leu Cys Ser Leu Val Thr Asp Phe Pro Gln Gly
        290                 295                 300

Val Arg Glu Cys Arg Glu Pro Glu Leu Gly Leu Glu Glu Leu Leu Arg
305                 310                 315                 320

His Arg Cys Gln Leu Leu Gln Gln Arg Glu Glu Tyr Gln Glu Glu Leu
                325                 330                 335

Glu Phe Cys Glu Lys Leu Leu Gln Thr Cys Phe Ser Ser Pro Thr Asp
            340                 345                 350

Asp Ser Met Asp Arg
            355

<210> SEQ ID NO 3
<211> LENGTH: 359
<212> TYPE: PRT
<213> ORGANISM: Homo sapiens

<400> SEQUENCE: 3

Met Ser Asp Glu Gly Ser Arg Gly Ser Arg Leu Pro Leu Ala Leu Pro
1               5                   10                  15

Pro Ala Ser Gln Gly Cys Ser Ser Gly Gly Gly Gly Gly Ser Ser
            20                  25                  30

Ala Gly Gly Ser Gly Asn Ser Arg Pro Pro Arg Asn Leu Gln Gly Leu
        35                  40                  45

Leu Gln Met Ala Ile Thr Ala Gly Ser Glu Glu Pro Asp Pro Pro
    50                  55                  60

Glu Pro Met Ser Glu Glu Arg Arg Gln Trp Leu Gln Glu Ala Met Ser
65                  70                  75                  80

Ala Ala Phe Arg Gly Gln Arg Glu Glu Val Glu Gln Met Lys Ser Cys
                85                  90                  95

Leu Arg Val Leu Ser Gln Pro Met Pro Pro Thr Ala Gly Glu Ala Glu
            100                 105                 110

Gln Ala Ala Asp Gln Gln Glu Arg Glu Gly Ala Leu Glu Leu Leu Ala
        115                 120                 125

Asp Leu Cys Glu Asn Met Asp Asn Ala Ala Asp Phe Cys Gln Leu Ser
    130                 135                 140

Gly Met His Leu Leu Val Gly Arg Tyr Leu Glu Ala Gly Ala Ala Gly
145                 150                 155                 160

Leu Arg Trp Arg Ala Ala Gln Leu Ile Gly Thr Cys Ser Gln Asn Val
                165                 170                 175

Ala Ala Ile Gln Glu Gln Val Leu Gly Leu Gly Ala Leu Arg Lys Leu
            180                 185                 190
```

```
Leu Arg Leu Leu Asp Arg Asp Ala Cys Asp Thr Val Arg Val Lys Ala
        195                 200                 205
Leu Phe Ala Ile Ser Cys Leu Val Arg Glu Gln Glu Ala Gly Leu Leu
        210                 215                 220
Gln Phe Leu Arg Leu Asp Gly Phe Ser Val Leu Met Arg Ala Met Gln
225                 230                 235                 240
Gln Gln Val Gln Lys Leu Lys Val Lys Ser Ala Phe Leu Leu Gln Asn
                245                 250                 255
Leu Leu Val Gly His Pro Glu His Lys Gly Thr Leu Cys Ser Met Gly
                260                 265                 270
Met Val Gln Gln Leu Val Ala Leu Val Arg Thr Glu His Ser Pro Phe
            275                 280                 285
His Glu His Val Leu Gly Ala Leu Cys Ser Leu Val Thr Asp Phe Pro
        290                 295                 300
Gln Gly Val Arg Glu Cys Arg Glu Pro Glu Leu Gly Leu Glu Glu Leu
305                 310                 315                 320
Leu Arg His Arg Cys Gln Leu Leu Gln Gln His Glu Glu Tyr Gln Glu
                325                 330                 335
Glu Leu Glu Phe Cys Glu Lys Leu Leu Gln Thr Cys Phe Ser Ser Pro
            340                 345                 350
Ala Asp Asp Ser Met Asp Arg
            355
```